(12) United States Patent
Yamada

(10) Patent No.: US 10,158,188 B2
(45) Date of Patent: Dec. 18, 2018

(54) CABLE CONNECTION STRUCTURE, ULTRASONIC PROBE, AND ULTRASONIC ENDOSCOPE SYSTEM

(71) Applicant: OLYMPUS CORPORATION, Tokyo (JP)

(72) Inventor: Junya Yamada, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 1095 days.

(21) Appl. No.: 14/494,980

(22) Filed: Sep. 24, 2014

(65) Prior Publication Data
US 2015/0011891 A1 Jan. 8, 2015

Related U.S. Application Data
(63) Continuation of application No. PCT/JP2013/053118, filed on Feb. 8, 2013.

(30) Foreign Application Priority Data
Mar. 27, 2012 (JP) .................................. 2012-072197

(51) Int. Cl.
*H01B 7/08* (2006.01)
*H05K 1/11* (2006.01)
(Continued)

(52) U.S. Cl.
CPC ............. *H01R 13/447* (2013.01); *A61B 8/12* (2013.01); *A61B 8/445* (2013.01); *A61B 8/4494* (2013.01); *G01N 29/24* (2013.01); *G01N 29/32* (2013.01); *H01R 12/598* (2013.01); *H01R 13/655* (2013.01); *H01R 35/02* (2013.01); *H05K 1/0215* (2013.01); *H05K 1/111* (2013.01); *A61B 1/00114* (2013.01); *A61B 1/00124* (2013.01);
(Continued)

(58) Field of Classification Search
CPC ............... H01B 7/08; H05K 1/11; H05K 7/00
USPC .............................. 174/117 F, 251, 267, 268
See application file for complete search history.

(56) References Cited

U.S. PATENT DOCUMENTS 5,262,590 A * 11/1993 Lia ........................ H01B 7/0861
156/55
5,374,321 A * 12/1994 Gatenby ................. C22C 21/00
148/418
(Continued)

FOREIGN PATENT DOCUMENTS

| JP | S49-10082 U | 1/1974 |
| JP | S58-116262 U | 8/1983 |

(Continued)

OTHER PUBLICATIONS

International Search Report dated May 7, 2013 issued in PCT/JP2013/053118.
(Continued)

*Primary Examiner* — Chau N Nguyen
(74) *Attorney, Agent, or Firm* — Scully, Scott, Murphy & Murphy, P.C.

(57) ABSTRACT

A cable connection structure for connecting a plurality of cables to an electrode provided on a substrate includes an extended portion that is provided integrally with the plurality of cables, extends from the plurality of cables, and covers at least a connection part between the plurality of cables and the electrode.

11 Claims, 13 Drawing Sheets

(51) Int. Cl.
*H01R 13/447* (2006.01)
*G01N 29/24* (2006.01)
*G01N 29/32* (2006.01)
*H01R 12/59* (2011.01)
*A61B 8/12* (2006.01)
*A61B 8/00* (2006.01)
*H01R 13/655* (2006.01)
*H01R 35/02* (2006.01)
*H05K 1/02* (2006.01)
*H01R 12/61* (2011.01)
*A61B 1/00* (2006.01)

(52) U.S. Cl.
CPC ...... *G01N 2291/2636* (2013.01); *H01R 12/61* (2013.01)

(56) References Cited

U.S. PATENT DOCUMENTS

| | | | | |
|---|---|---|---|---|
| 5,375,321 | A * | 12/1994 | Rohatgi | H05K 1/0218 29/830 |
| 6,927,343 | B2 * | 8/2005 | Watanabe | G01R 1/07314 174/117 F |
| 2001/0050184 | A1 * | 12/2001 | Adachi | H01R 4/02 174/268 |
| 2002/0189854 | A1 * | 12/2002 | Crumly | H05K 1/0281 174/254 |

FOREIGN PATENT DOCUMENTS

| | | |
|---|---|---|
| JP | S61-117265 U | 7/1986 |
| JP | S62-63979 U | 4/1987 |
| JP | H02-111410 U | 9/1990 |
| JP | H03-151942 A | 6/1991 |
| JP | H04-287397 A | 10/1992 |
| JP | 05-136593 A | 6/1993 |
| JP | 08-330682 A | 12/1996 |
| JP | 2000-067968 A | 3/2000 |
| JP | 2003-309339 A | 10/2003 |
| JP | 2009-194934 A | 8/2009 |
| JP | 2009-239976 A | 10/2009 |

OTHER PUBLICATIONS

Decision to Grant a Patent dated Mar. 21, 2017 in Japanese Patent Application No. 2016-110338.
Japanese Office Action dated Apr. 5, 2016 in related Japanese Patent Application No. 2012-072197.

* cited by examiner

CABLE CONNECTION STRUCTURE, ULTRASONIC PROBE, AND ULTRASONIC ENDOSCOPE SYSTEM

CROSS REFERENCES TO RELATED APPLICATIONS

This application is a continuation of PCT international application Ser. No. PCT/JP2013/053118 filed on Feb. 8, 2013 which designates the United States, incorporated herein by reference, and which claims the benefit of priority from Japanese Patent Application No. 2012-072197, filed on Mar. 27, 2012, incorporated herein by reference.

BACKGROUND

1. Technical Field

The disclosure relates to a cable connection structure for connecting a cable to a substrate, and an ultrasonic probe and an ultrasonic endoscope system to which the cable connection structure is applied.

2. Related Art

Conventionally, as a connection structure of a coaxial cable for connecting the coaxial cable to a substrate provided with an electrode, there has been disclosed a technique of covering an exposed part of the connector connected to the substrate, with a flexible printed circuit (FPC) which is fixed to the substrate by solder (see JP 5-136593 A, for example). According to the technique disclosed in JP 5-136593 A, it is possible to shield an electromagnetic wave that enters the connection structure from outside, with a simple configuration.

There is also disclosed a technique in which an FPC as a substrate on which a semiconductor component is mounted, has an extended part, and it is possible to provide shading and shielding by bending the extended part to cover the semiconductor component (see JP 3234743 B1, for example). According to the technique disclosed in JP 3234743 B1, since the semiconductor component is integrally covered with the extended part, it is possible to shield a noise incident from outside and a noise radiated from inside with a much simpler configuration than that of the technique disclosed in JP 5-136593 A in which a separate member is used for the shielding.

SUMMARY

In accordance with some embodiments, a cable connection structure, an ultrasonic probe and an ultrasonic endoscope system are presented.

In some embodiments, a cable connection structure for connecting a plurality of cables to an electrode provided on a substrate includes an extended portion that is provided integrally with the plurality of cables, extends from the plurality of cables, and covers at least a connection part between the plurality of cables and the electrode.

In some embodiments, an ultrasonic probe includes: a plurality of cables; a substrate on which an electrode is provided; a transducer module having a plurality of ultrasonic transducers mounted on the substrate; and an extended portion that is provided integrally with the plurality of cables, extends from the plurality of cables, and covers at least a connection part between the plurality of cables and the electrode.

In some embodiments, an ultrasonic endoscope system includes: an insertion unit configured to be inserted into a body of a subject to output an ultrasonic signal in the body and to obtain the ultrasonic signal reflected from the body; and the above-described ultrasonic probe provided at a distal end of the insertion unit.

The above and other features, advantages and technical and industrial significance of this invention will be better understood by reading the following detailed description of presently preferred embodiments of the invention, when considered in connection with the accompanying drawings.

DETAILED DESCRIPTION

Figure 1:
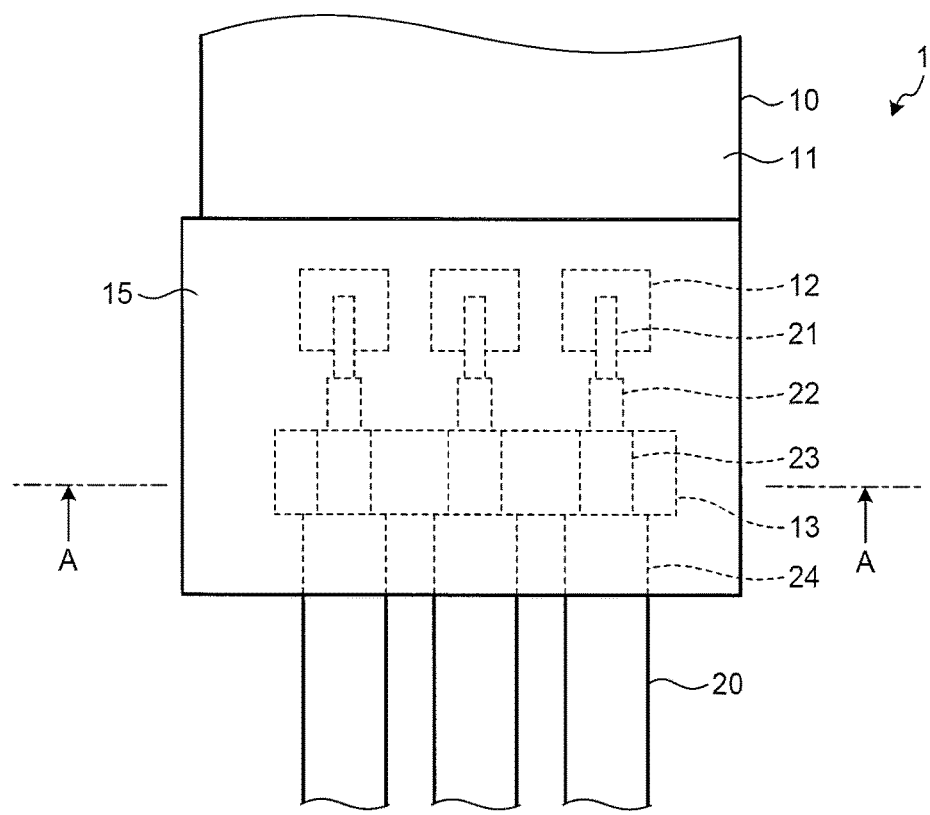
FIG. 1 is a schematic view illustrating a cable connection structure according to a first embodiment of the present invention.

Exemplary embodiments for carrying out the invention will be described below in detail with reference to the drawings. Note that the invention is not to be limited by the embodiments below. Each of the drawings referenced in descriptions below only schematically illustrates a shape, a size, and a positional relationship to a degree that enables understanding of content of the invention. That is, the invention is not to be limited only to the shape, the size, and the positional relationship exemplified in each of the drawings. The same reference numerals are used to refer to the same elements throughout the drawings.

First Embodiment

Figure 2:
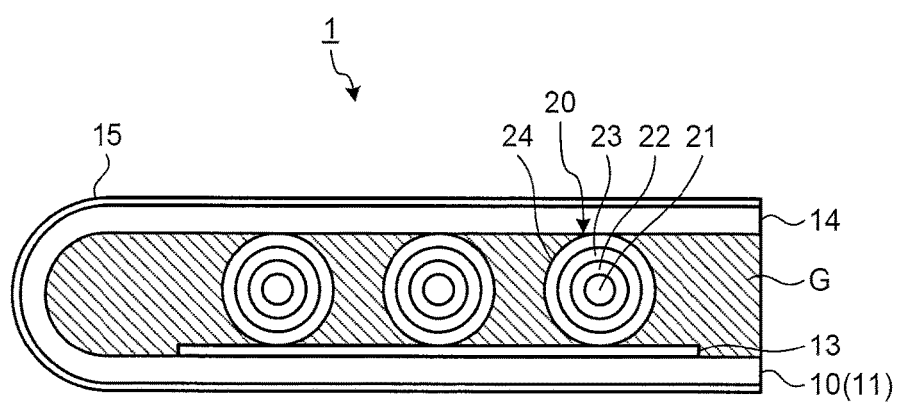
FIG. 2 is a partial sectional view of an electronic device illustrated in FIG. 1 taken along line A-A.
Figure 3:
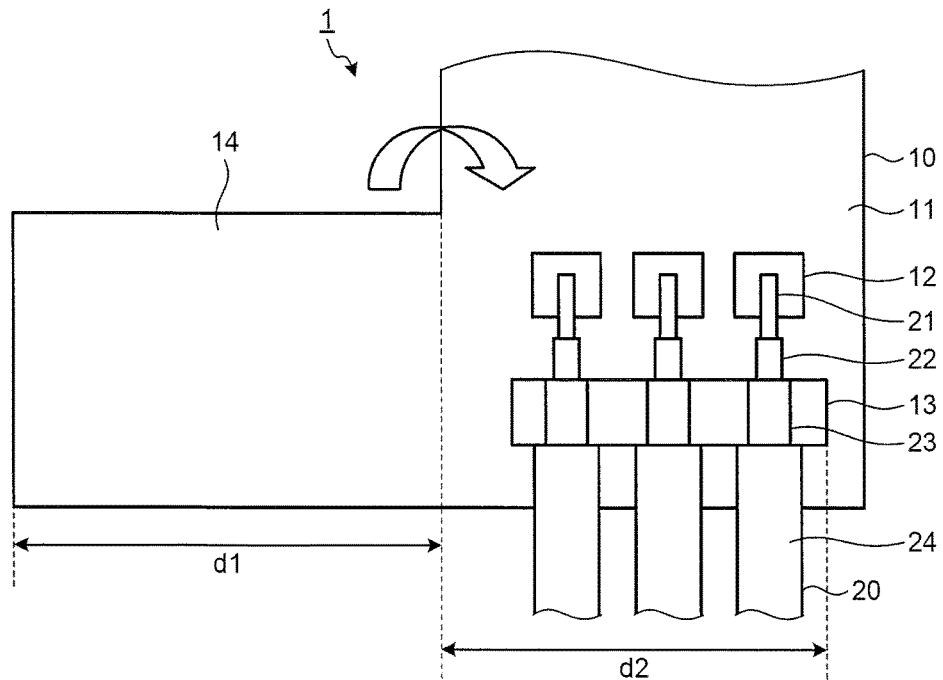
FIG. 3 is a schematic view illustrating the cable connection structure according to the first embodiment of the present invention.

FIG. 1 is a schematic view illustrating a cable connection structure according to a first embodiment. FIG. 2 is a partial sectional view of an electronic device illustrated in FIG. 1 taken along line A-A. FIG. 3 is a schematic view illustrating the cable connection structure according to the first embodiment. As illustrated in FIG. 1, a cable connection structure 1 according to the first embodiment includes a substrate 10, and a plurality of cables 20 connected to the substrate 10. Hereinafter, note that the cables 20 are described as being coaxial cables.

The substrate 10 is a FPC constituted by a bendable insulation film and has a substantially rectangular circuit formed portion 11 where an electric circuit, an electrode, and the like are formed, and electrodes 12 and 13 electrically connected to the cables 20, respectively, on one of surfaces thereof. The substrate 10 includes an extended portion 14, which is constituted by a bendable insulation film and extending from an edge portion of the circuit formed portion 11, and a ground electrode 15, which is provided on a surface on a side different from a side where the cables 20 are connected and contains copper and the like. Here, the electrode 12 is a core wire connection electrode connecting to a core wire 21 of the cable 20, described below, while the electrode 13 is a shield wire connection electrode connecting to a shield wire 23. The substrate 10 is electrically grounded through the ground electrode 15. Note that it is also possible to provide the ground electrode 15 inside the insulation film as long as it is positioned on the outermost side on the surface on the side different from the side where the cables 20 are connected.

The cable 20 includes: the core wire 21 formed of a conductor containing copper and the like; an internal insulating layer 22 that is constituted by an insulator, covers an outer periphery of the core wire 21, and exposes the core wire 21 on a distal end side; the shield wire 23 constituted by a conductor covering an outer periphery of the internal insulating layer 22; and an external insulating layer 24 constituted by an insulator covering an outer periphery of the shield wire 23. The cable 20 is denuded of the internal insulating layer 22, the shield wire 23, and the external insulating layer 24 at an edge portion thereof on a side where the substrate is connected.

In the substrate 10 and the cable 20, the electrode 12 is electrically connected to the core wire 21 by a conductive joining material such as solder. With regard to the electrode 13 and the shield wire 23 as well, the electrode 13 is electrically connected to the shield wire 23 by the conductive joining material such as the solder.

On the substrate 10, the plurality of cables 20 is disposed according to an arrangement of each of the electrodes 12. Here, in a case where the electrodes 12 are arranged in a line as illustrated in FIGS. 1 and 2, the extended portion 14 is extended in an array direction of the electrodes 12 (see FIG. 3). A distance d1 in the array direction from a proximal end of the extended portion 14 is at least equal to or greater than a distance to an edge portion of a member that is located farthest among the electrodes 12 and 13 and the cables 20 from the proximal end (in the first embodiment, a distance d2 to an edge portion of the electrode 13). At this time, it is preferred that the distance d1 be determined by taking into account the thickness of the cables 20 and the electrodes 12 and 13.

A distance of the extended portion 14 in a direction orthogonal to the array direction is equal to or greater than a distance to an edge portion that is located farthest among edge portions of the electrodes 12 or the core wires 21 from a proximal end in the direction orthogonal to the array direction. It is preferred that the distance be determined by taking into account the thickness of the cables 20 and the electrodes 12 and 13.

The extended portion 14 is bent at the proximal end in the array direction to cover the electrodes 12 and 13 and the cables 20. Accordingly, with a simple configuration, it is possible to prevent damage to the electrodes 12 and 13 and the cables 20 as well as to shield a noise incident from outside and a noise radiated from inside. Since the ground electrode is provided on an outer surface side of a region covered by the extended portion 14, it is possible to secure required insulation even in a case where the outside of the cable connection structure 1 is damaged.

Here, as illustrated in FIG. 2, adhesive G (fixing member) made of an insulating resin is filled between the circuit formed portion 11, the extended portion 14, and the cables 20, whereby a positional relationship therebetween is fixed. Since the positional relationship is fixed by the adhesive G being filled between the circuit formed portion 11, the extended portion 14, and the cables 20, it is possible to hold a distance between a signal wire of each of the cables 20 and the ground electrode 15 covering the outer surface of the extended portion 14 appropriately. Therefore, it is possible to suppress interference between signals transmitted through each of the cables 20.

According to the first embodiment, the substrate 10 constituted by an bendable insulation film includes the extended portion 14, which covers the electrodes 12 and 13 and the cables 20, and the adhesive G is filled in a space formed by the extended portion 14, whereby with a simple configuration, it is possible to shield the noise incident from outside and the noise radiated from inside as well as to suppress interference of signals between the cables.

Note that in the above-described first embodiment, the adhesive G is filled in the space formed by the circuit formed portion 11, the extended portion 14, and the cables 20; however, it is also possible to provide the adhesive G partially as long as it is capable of fixing the positional relationship between the circuit formed portion 11, the extended portion 14, and the cables 20 and is arranged so as to cover the cables 20. Furthermore, as long as the electrode 12 and the core wire 21 as well as the electrode 13 and the shield wire 23 are fixed by the conductive joining material, and the interference of the signals between the cables is suppressed by the ground electrode 15 and the like, it is also possible that the adhesive G only fix between the circuit formed portion 11 and the extended portion 14. As the adhesive G, any resin and the like having an insulating property and being capable of fixing the positional relationship between the circuit formed portion 11, the extended portion 14, and the cable 20 are applicable.

In the above-described first embodiment, the ground electrode 15 covers an outer surface side of the circuit formed portion 11 and the extended portion 14 entirely; however, as long as it is capable of being grounded, the ground electrode 15 may cover a part of the outer surface side of the circuit formed portion 11 and the extended portion 14. The ground electrode 15 may also be provided in accordance with a connection part of the substrate 10 and the cable 20.

The above-described first embodiment exemplifies a case in which a coaxial cable is connected to the substrate; however, it is not limited to this case and is also applicable to different types of cables besides the coaxial cable.

Figure 4:
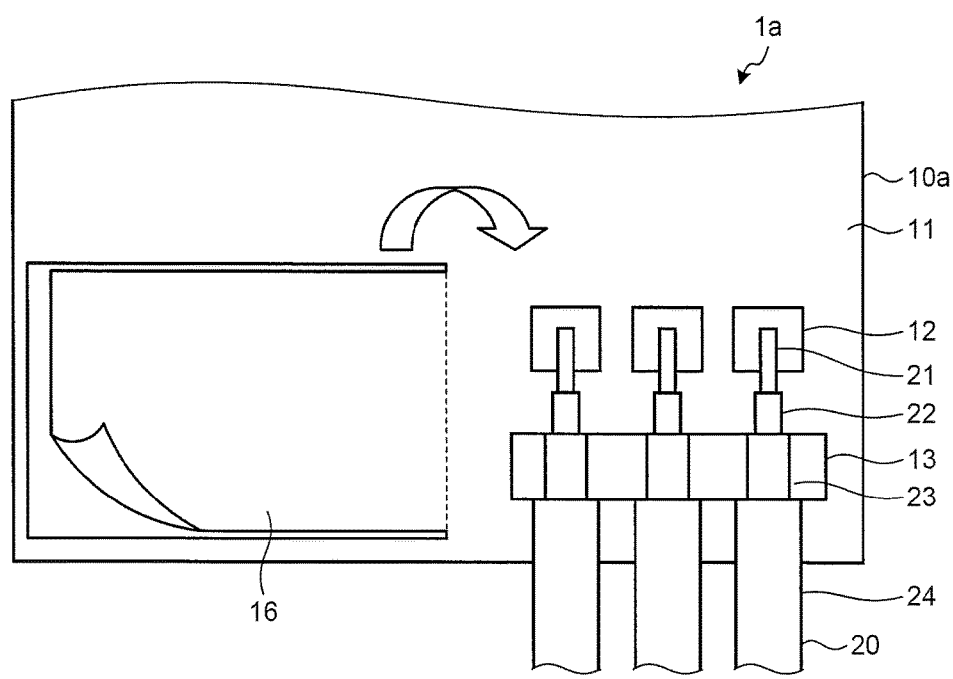
FIG. 4 is a schematic view illustrating a cable connection structure according to a modified example 1-1 of the first embodiment of the present invention.
Figure 5:
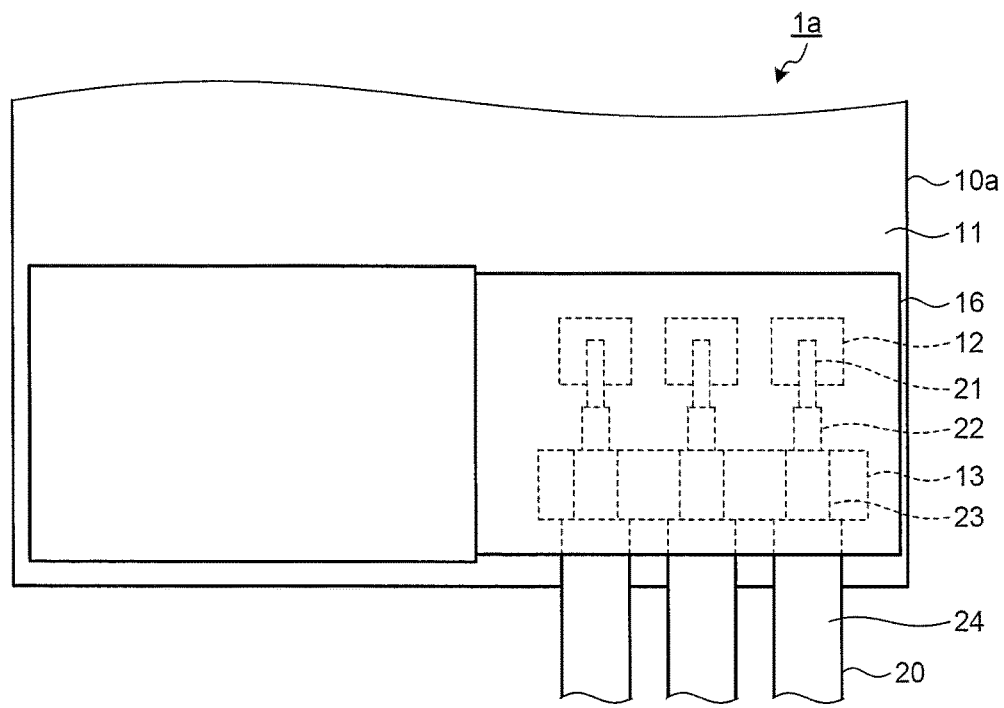
FIG. 5 is a schematic view illustrating the cable connection structure according to the modified example 1-1 of the first embodiment of the present invention.

FIG. 4 is a schematic view illustrating a cable connection structure 1a according to a modified example 1-1 of the first embodiment. FIG. 5 is a schematic view illustrating the cable connection structure 1a according to the modified example 1-1 of the first embodiment. As in the cable connection structure 1a illustrated in FIG. 4, an extended portion 16 may be formed by making a C-shaped cutting in a region adjacent to the circuit formed portion 11 in a substrate 10a constituted by a bendable insulation film. Accordingly, it is possible to integrally provide the substrate 10a with the extended portion 16 constituted by a bendable insulation film.

The extended portion 16 is provided by making the C-shaped cutting in the substrate 10a in the array direction of the electrodes 12 of the circuit formed portion 11. At this time, in the extended portion 16, a straight line connecting both ends of a C shape (proximal end, or a broken line in FIG. 4) is on a side of the circuit formed portion 11 and is substantially orthogonal to the array direction of the electrodes 12.

The extended portion 16 is bent at the proximal end in the array direction to cover the electrodes 12 and 13 and the cables 20 (see FIG. 5). Accordingly, similar to the above-described first embodiment, with a simple configuration, it is possible to prevent damage to the electrodes 12 and 13 and the cables 20 as well as to shield a noise incident from outside and a noise radiated from inside.

By filling the inside with adhesive and by providing a ground electrode on an outer surface side in a state where the extended portion 16 is bent, a positional relationship between the circuit formed portion 11, the extended portion 16, and the cables 20 is fixed, whereby it is possible to hold a distance between the signal wire of each of the cables 20 and the ground electrode formed in the extended portion 16 appropriately. Therefore, it is possible to suppress interference between signals transmitted through each of the cables 20 and to secure required insulation even in a case where the outside of the cable connection structure 1a is damaged.

Second Embodiment

Figure 6:
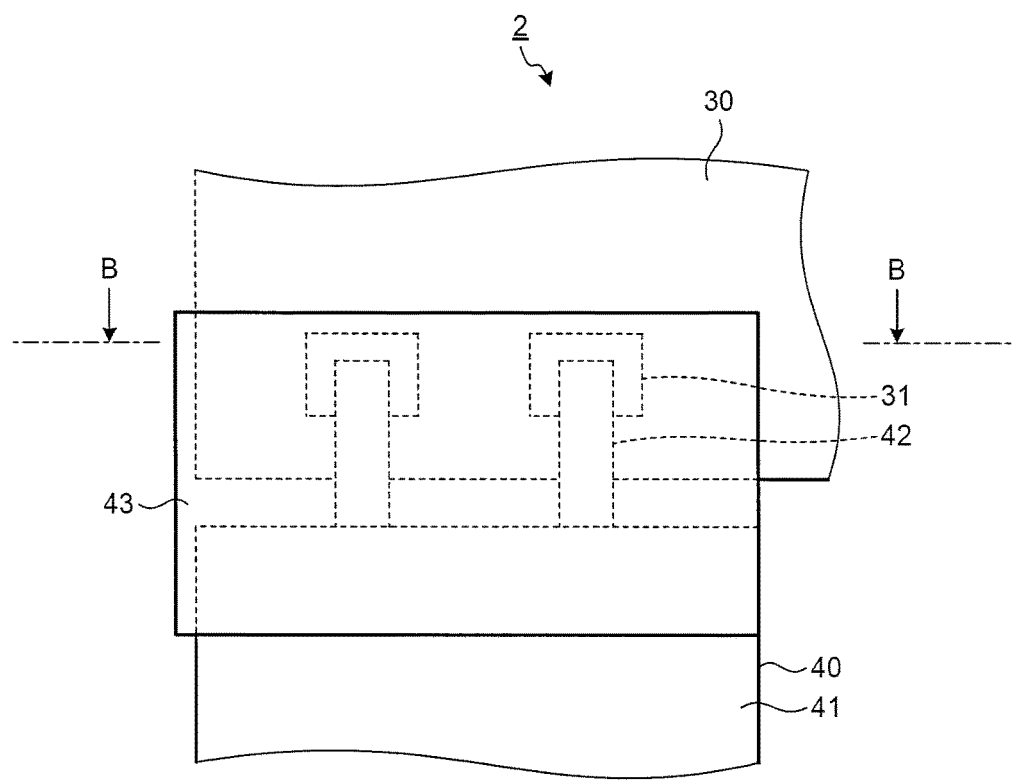
FIG. 6 is a schematic view illustrating a cable connection structure according to a second embodiment of the present invention.
Figure 7:
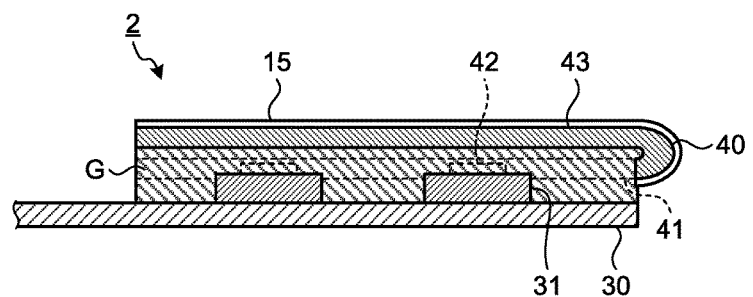
FIG. 7 is a sectional view of the cable connection structure illustrated in FIG. 6 taken along line B-B.
Figure 8:
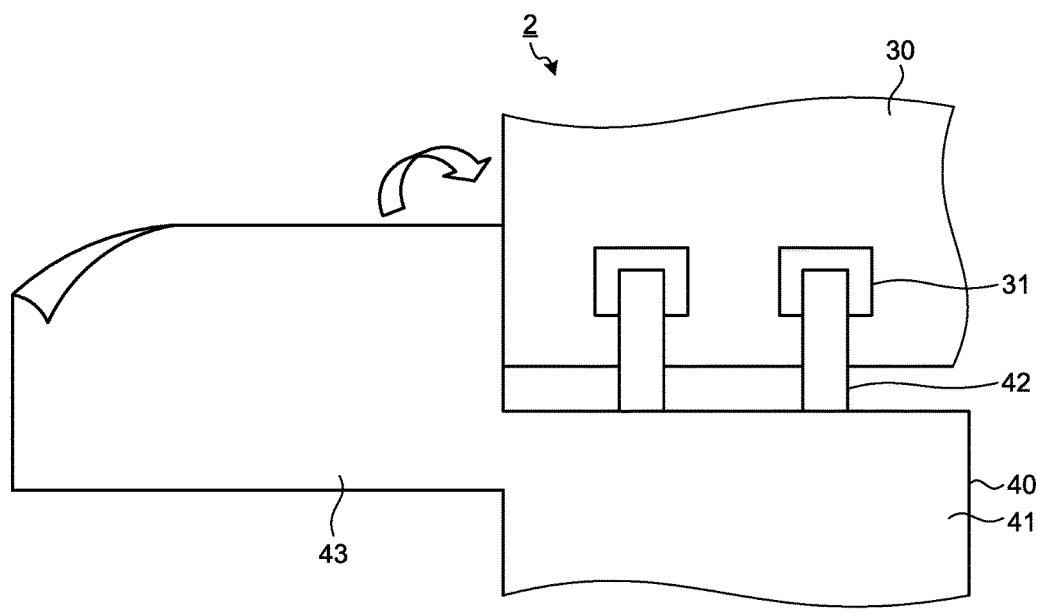
FIG. 8 is a schematic view illustrating the cable connection structure according to the second embodiment of the present invention.

FIG. 6 is a schematic view illustrating a cable connection structure according to a second embodiment. FIG. 7 is a sectional view taken along line B-B of the cable connection structure illustrated in FIG. 6. FIG. 8 is a schematic view illustrating the cable connection structure according to the second embodiment. A cable connection structure 2 according to the second embodiment, as illustrated in FIG. 6, includes a substrate 30, and an FPC substrate 40 having a plurality of lead terminals 42 (cables) connected to the substrate 30. The substrate 30 is constituted by a semiconductor and a glass epoxy resin, for example, and has a substantially rectangular shape. An electric circuit and a plurality of electrodes 31, which is connected to this electric circuit and is provided on one of surfaces, are formed thereon.

The FPC substrate 40 is constituted by a bendable insulation film and has a substantially rectangular circuit formed portion 41, which is a region where an electric circuit and the like are formed, and a plurality of lead terminals 42, which is connected to the circuit formed portion 41 and projects from one end of the circuit formed portion 41. The FPC substrate 40 includes an extended portion 43, which is constituted by a bendable insulation film and extends from one end of the circuit formed portion 41. The lead terminal 42 is formed of copper, for example, and a surface thereof may be plated with nickel and gold.

On the substrate 30 and the FPC substrate 40, the electrode 31 is electrically connected to the lead terminal 42 by, for example, a conductive joining material such as solder. It may also be electrically connected by metallic bonding of electrodes such as in ultrasonic joining.

In a case where the plurality of lead terminals 42 is arranged in a line on the FPC substrate 40, the extended portion 43 extends in an array direction of the lead terminals 42. As in the first embodiment, a distance in the array direction from a proximal end of the extended portion 43 is at least equal to or greater than a distance to an edge portion of a member that is located farthest among the electrodes 31 or the lead terminals 42 from the proximal end of the extended portion 43 (in the second embodiment, a distance to an edge portion of the electrode 31). At this time, it is preferred that the distance be determined by taking into account the thickness of the electrode 31 or the lead terminal 42.

In the extended portion 43, a length orthogonal to the array direction is a length sufficient to cover the electrode 31 and the lead terminal 42 when the electrode 31 and the lead terminal 42 are connected (fixed).

The extended portion 43 is bent at the proximal end to cover the electrode 31 and the lead terminal 42. Accordingly, in the second embodiment, similar to the above-described first embodiment, with a simple configuration, it is possible to prevent damage to the electrode 31 and the lead terminal 42 as well as to shield a noise incident from outside and a noise radiated from inside.

In a state where the extended portion 43 is bent, by fixing the extended portion 43 and the substrate 30 with adhesive and by providing a ground electrode on an outer surface side thereof, a positional relationship between the extended portion 43 and the substrate 30 is fixed, whereby it is possible to hold a distance between each of the lead terminals 42 and the ground electrode formed in the extended portion 43 appropriately. Therefore, it is possible to suppress interference between signals transmitted through each of the lead terminals 42, and it is possible to secure required insulation even in a case where the outside of the cable connection structure 2 is damaged.

Figure 9:
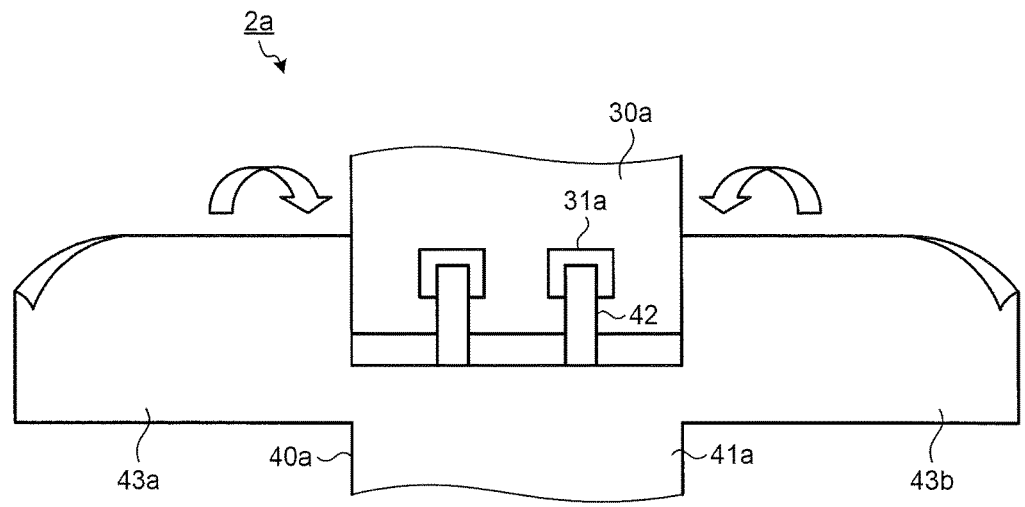
FIG. 9 is a schematic view illustrating a cable connection structure according to a modified example 2-1 of the second embodiment of the present invention.
Figure 10:
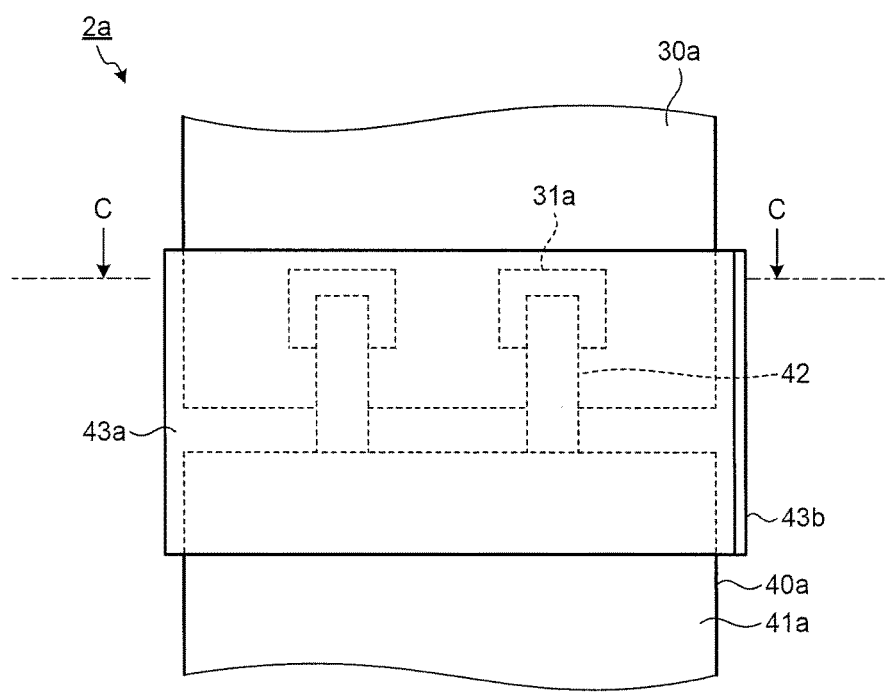
FIG. 10 is a schematic view illustrating the cable connection structure according to the modified example 2-1 of the second embodiment of the present invention.
Figure 11:
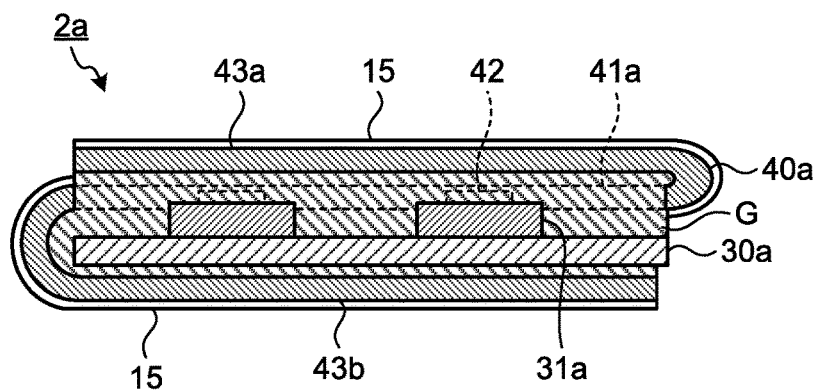
FIG. 11 is a sectional view of the cable connection structure illustrated in FIG. 10 taken along line C-C.

FIG. 9 is a schematic view illustrating a cable connection structure according to a modified example 2-1 of the second embodiment. FIG. 10 is a schematic view illustrating the cable connection structure according to the modified example 2-1 of the second embodiment. FIG. 11 is a sectional view of the cable connection structure illustrated in FIG. 10 taken along line C-C. In the above-described second embodiment, it has been described that one extended portion is provided; however, it is also possible to provide more than one extended portion.

As illustrated in FIGS. 9 to 11, a cable connection structure 2a according to the modified example 2-1 includes a substrate 30a and an FPC substrate 40a having a plurality of lead terminals 42 connected to the substrate 30a. The substrate 30a is constituted by a semiconductor and a glass epoxy resin, for example, and has a substantially rectangular shape. An electric circuit and a plurality of electrodes 31a, which is connected to this electric circuit and is provided on one of surfaces, are formed thereon.

The FPC substrate 40a is constituted by a bendable insulation film and has a substantially rectangular circuit formed portion 41a, which is a region where an electric circuit and the like are formed, and the plurality of lead terminals 42, which is connected to the circuit formed portion 41a and projects from one end of the circuit formed portion 41a. The FPC substrate 40a includes two extended portions 43a and 43b, each of which is constituted by a bendable insulation film and extends from the circuit formed portion 41a.

On the substrate 30a and the FPC substrate 40a, the electrode 31a is electrically connected to the lead terminal 42 by, for example, a conductive joining material such as solder. It may also be electrically connected by metallic bonding of electrodes such as in ultrasonic joining.

In a case where the plurality of lead terminals 42 is arranged in a line on the FPC substrate 40a, each of the two extended portions 43a and 43b extends along an array direction of the lead terminals 42 from a side surface perpendicular to a side surface from which the lead terminals 42 of the circuit formed portion 41a project. As in the second embodiment, a distance in the array direction from a proximal end of each of the two extended portions 43a and 43b is at least equal to or greater than a distance to an edge portion of a member that is located farthest among the electrodes 31a or the lead terminals 42 from the proximal end of the extended portion 43a or the extended portion 43b. At this time, it is preferred that the distance be determined by taking into account the thickness of the electrode 31a and the lead terminal 42.

In the two extended portions 43a and 43b, a length orthogonal to the array direction is a length sufficient to cover the electrode 31a and the lead terminal 42 in a state where the electrode 31a and the lead terminal 42 are connected (fixed).

Each of the two extended portions 43a and 43b is bent at the proximal end to cover a surface of the substrate 30a. At this time, one of the extended portions (for example, the extended portion 43a) covers a surface on which the electrode 31a of the substrate 30a and the lead terminal 42 are arranged. The other of the extended portions (for example, the extended portion 43b) covers the back of the surface on which the electrode 31a of the substrate 30a and the lead terminal 42 are arranged (see FIG. 11). Accordingly, in the modified example 2-1, it is possible to prevent the damage of the substrate 30a more certainly than in the above-described second embodiment as well as to shield a noise incident from outside and a noise radiated from inside.

In a state where the two extended portions 43a and 43b are bent, by fixing each of the extended portions 43a and 43b and the substrate 30a with adhesive and by providing a ground electrode on an outer surface side thereof, a positional relationship between each of the extended portions 43a and 43b and the substrate 30a is fixed, whereby it is possible to hold a distance between each of the lead terminals 42 and the ground electrode formed in the extended portions 43a and 43b appropriately. Therefore, it is possible to suppress interference between signals transmitted through each of the lead terminals 42, and it is possible to secure required insulation even in a case where the outside of the cable connection structure 2a is damaged.

Note that in the above-described modified example 2-1, two extended portions 43a and 43b are provided; however, it is also possible to provide one extended portion, which has a length in accordance with the two extended portions and is wound around the substrate. Accordingly, it becomes possible to cover an outer periphery of the substrate with the extended portion.

Figure 12:
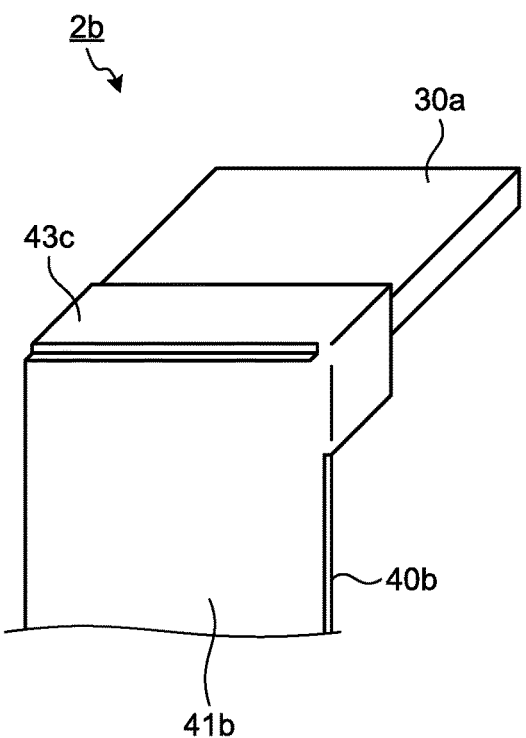
FIG. 12 is a perspective view schematically illustrating a cable connection structure of a modified example 2-2 of the second embodiment of the present invention.
Figure 13:
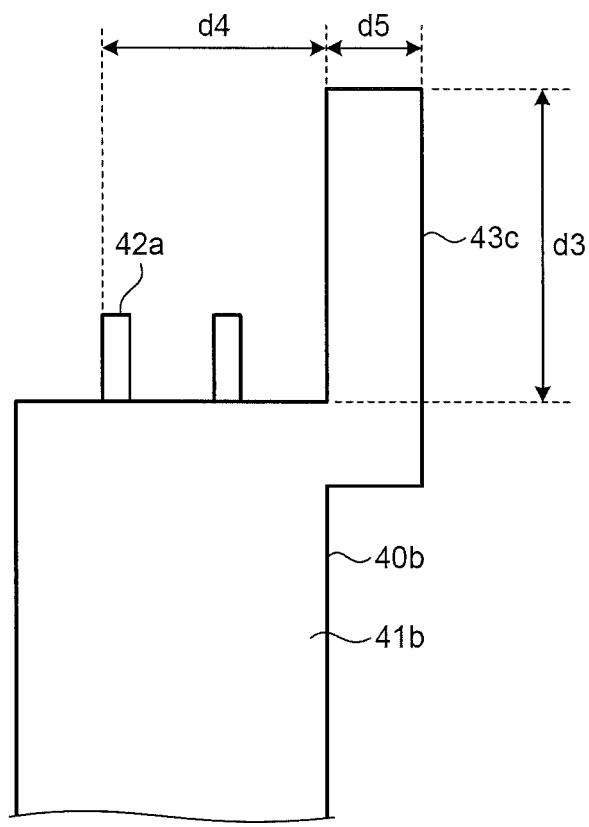
FIG. 13 is a schematic view illustrating a configuration of a substrate of the cable connection structure illustrated in FIG. 12.
Figure 14:
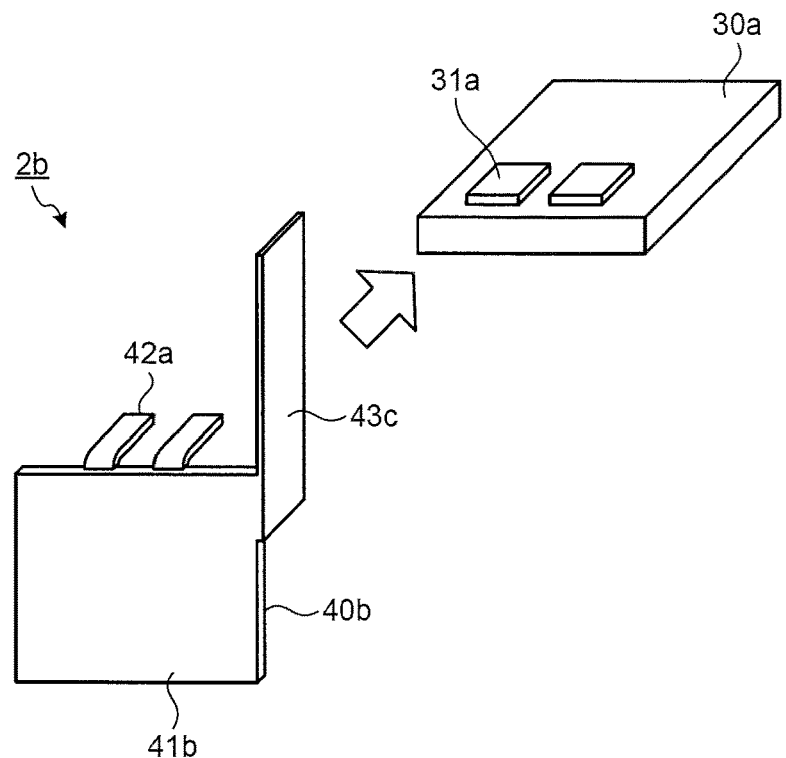
FIG. 14 is an exploded perspective view schematically illustrating the cable connection structure of the modified example 2-2 of the second embodiment of the present invention.
Figure 15:
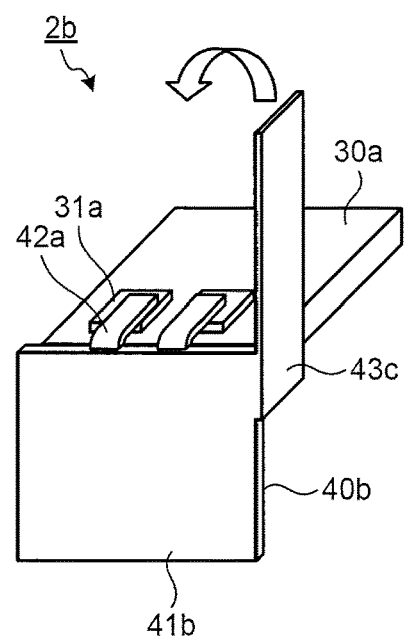
FIG. 15 is a perspective view schematically illustrating the cable connection structure of the modified example 2-2 of the second embodiment of the present invention.

FIG. 12 is a schematic perspective view illustrating a cable connection structure of a modified example 2-2 of the second embodiment. FIG. 13 is a schematic view illustrating a configuration of a substrate of the cable connection structure in FIG. 12. FIG. 14 is an exploded perspective view schematically illustrating the cable connection structure of the modified example 2-2 of the second embodiment. FIG. 15 is a perspective view schematically illustrating the cable connection structure of the modified example 2-2 of the second embodiment. In the above-described second embodiment, a principal surface of the substrate and a principal surface of the FPC substrate are substantially parallel to each other; however, the principal surface of the substrate may also be orthogonal to the principal surface of the FPC substrate.

A cable connection structure 2b according to the modified example 2-2 includes the above-described substrate 30a, and a FPC substrate 40b having a plurality of lead terminals 42a (cable) connected to the substrate 30a. The FPC substrate 40b is constituted by a bendable insulation film, and has a substantially rectangular circuit formed portion 41b on which an electric circuit and the like are formed, and the plurality of lead terminals 42a, which is connected to the circuit formed portion 41b and projects from one end of the circuit formed portion 41b. The FPC substrate 40b is also provided with an extended portion 43c, which is constituted by a bendable insulation film and extends from one end of the circuit formed portion 41b. The lead terminal 42a is formed of copper, for example, and a surface thereof may be plated with nickel and gold.

The extended portion 43c extends along a direction perpendicular to the array direction of the lead terminals 42a, and extends such that a distance d3 in a projection direction from a projection edge portion of the lead terminal 42a of the circuit formed portion 41b is at least equal to or greater than a distance d4, which is from an edge portion of the extended portion 43c on a lead terminal 42a side to an edge portion of the lead terminal 42a on a far side from the extended portion 43c. A projection length d5 from a proximal end of the extended portion 43c is a length with which it is possible to cover the lead terminal 42a and the electrode 31a when it is bent.

On the substrate 30a and the FPC substrate 40b, the electrode 31a is electrically connected to the lead terminal 42a by, for example, a conductive joining material such as solder. It may also be electrically connected by metallic bonding of electrodes such as in ultrasonic joining. At this time, as illustrated in FIG. 14, the lead terminal 42a is bent in a direction orthogonal to a principal surface of the circuit formed portion 41b and is connected to the electrode 31a.

When the lead terminal 42a is connected to the electrode 31a, a principal surface of the extended portion 43c is bent at a proximal end thereof in a direction orthogonal to the principal surface of the circuit formed portion 41b (see FIG.

15). Subsequently, it is bent along an outer edge of the substrate 30a to cover the electrode 31a and the lead terminal 42a (see FIG. 12).

At this time, it is preferred that a contact part between a side surface of the substrate 30a and the circuit formed portion 41b of the FPC substrate 40b be fixed with an adhesive and the like. According to the modified example 2-2, in addition to an effect according to the above-described second embodiment, it becomes applicable even in a case where the principal surface of the substrate 30a is not parallel to the principal surface of the FPC substrate 40b. By fixing the extended portion 43c and the substrate 30a with adhesive and by providing a ground electrode at least on an outer surface side of the extended portion 43c, a positional relationship between the extended portion 43c and the substrate 30a is fixed, whereby it is possible to hold a distance between each of the lead terminals 42a and the ground electrode formed in the extended portion 43c appropriately. Therefore, it is possible to suppress interference between signals transmitted through each of the lead terminals 42a, and it is possible to secure required insulation even in a case where the outside of the cable connection structure 2b is damaged.

Third Embodiment

Figure 16:
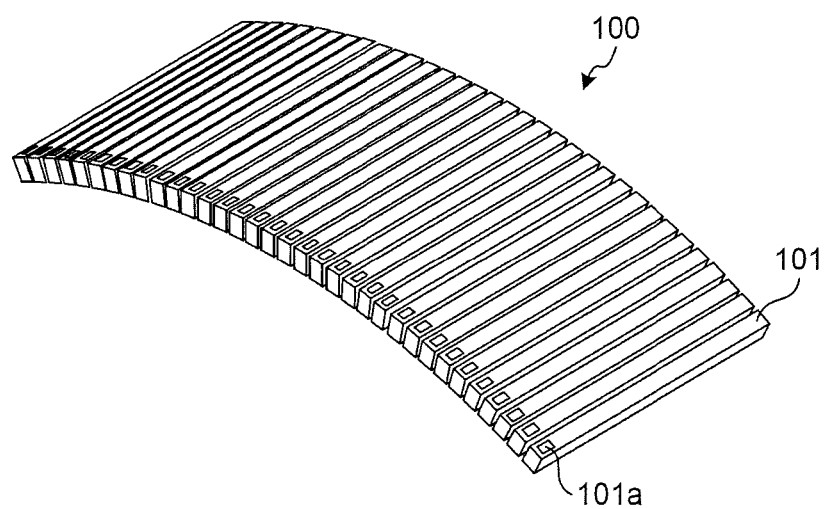
FIG. 16 is a schematic view illustrating a configuration of a transducer module to be connected to a cable connection structure according to a third embodiment of the present invention.
Figure 17:
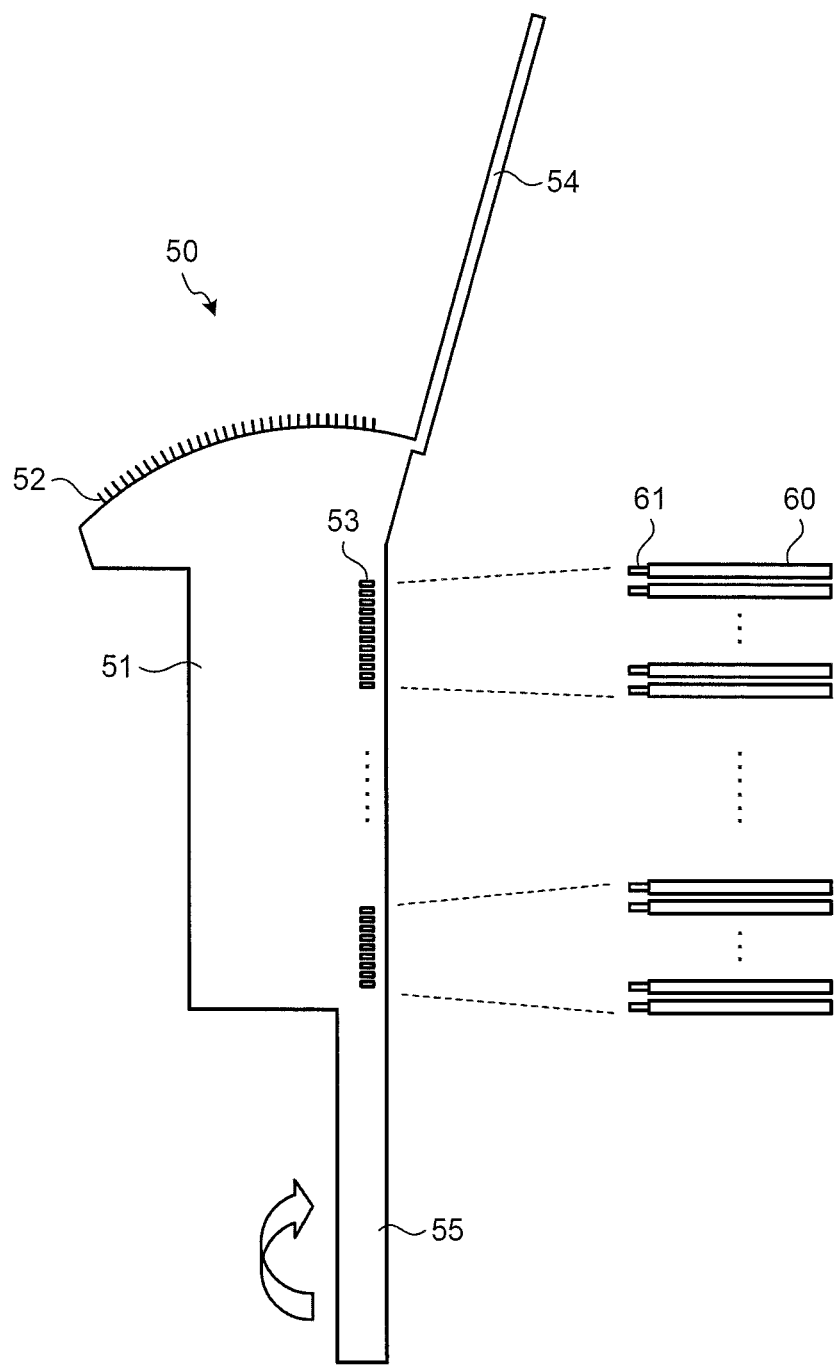
FIG. 17 is a schematic view illustrating a configuration of a substrate of the cable connection structure according to the third embodiment of the present invention.

FIG. 16 is a schematic view illustrating a configuration of a transducer module 100 connected to a cable connection structure according to a third embodiment. FIG. 17 is a schematic view illustrating a configuration of a FPC substrate 50 of the cable connection structure according to the third embodiment. The transducer module 100 used in the third embodiment, as illustrated in FIG. 16, has a polygonal column-shaped ultrasonic transducer 101, which is constituted by a piezoelectric element, for example. The plurality of ultrasonic transducers 101 is mounted on a substrate being arrayed in a direction orthogonal to a longitudinal direction of the ultrasonic transducer 101. Here, in the transducer module 100, a side surface formed by the plurality of ultrasonic transducers 101 that has been arrayed has an arc shape (convex type). Each of the ultrasonic transducers 101 includes an electrode 101a on one end side thereof for electrically connecting with, for example, the FPC substrate 50 illustrated in FIG. 17.

The FPC substrate 50 includes a circuit formed portion 51, which is constituted by a bendable insulation film and is a region where an electric circuit and the like are formed, a plurality of lead terminals 52 (cables) which projects from one end of the circuit formed portion 51, and electrodes 53 which are provided on a surface on the other end side of the circuit formed portion 51 and are connected to a plurality of cables 60, respectively. The FPC substrate 50 includes a first extended portion 54 which is constituted by a bendable insulation film and extends from an edge portion of the circuit formed portion 51 in the vicinity of the lead terminals 52, and a second extended portion 55 which extends from an edge portion of the circuit formed portion 51 in the vicinity of the electrodes 53. Here, an end face from which the lead terminals 52 project has the same curvature as a curvature of an arc-shaped side surface formed by the plurality of ultrasonic transducers 101. The lead terminal 52 is formed of copper, for example, and a surface thereof may be plated with nickel and gold.

Figure 18:
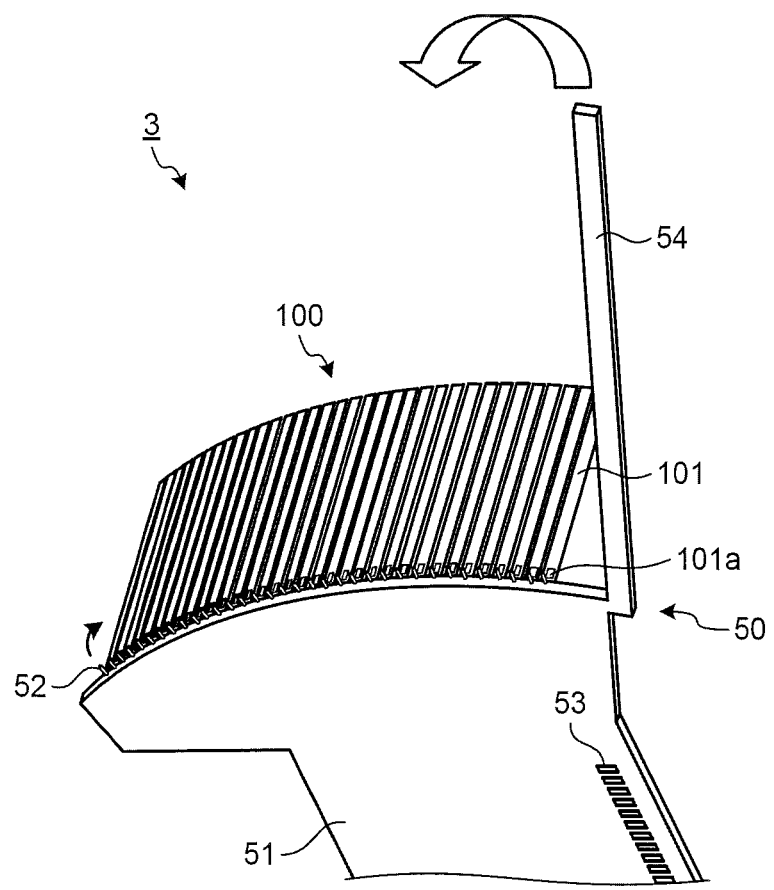
FIG. 18 is a perspective view schematically illustrating an ultrasonic probe including the cable connection structure according to the third embodiment of the present invention.
Figure 19:
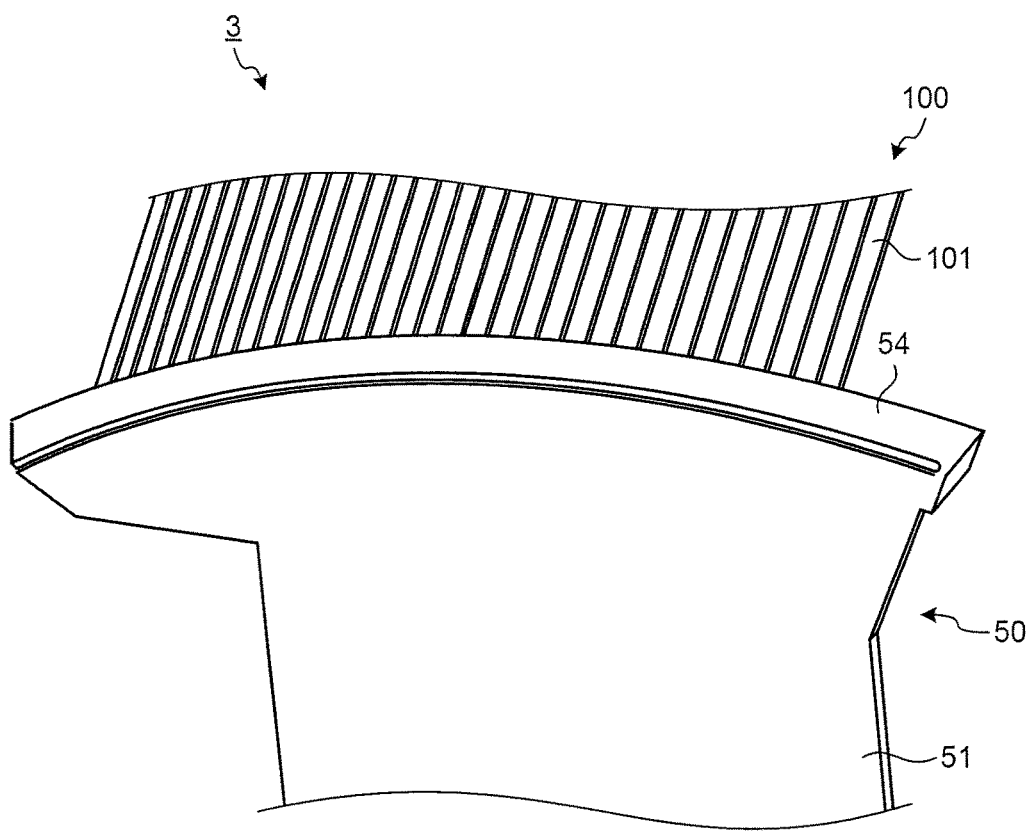
FIG. 19 is a perspective view schematically illustrating the ultrasonic probe including the cable connection structure according to the third embodiment of the present invention.

FIG. 18 is a perspective view schematically illustrating an ultrasonic probe 3 including the cable connection structure according to the third embodiment. FIG. 19 is a perspective view schematically illustrating the ultrasonic probe 3 including the cable connection structure according to the third embodiment. In a case where the transducer module 100 is electrically connected to the FPC substrate 50, as illustrated in FIG. 18, the lead terminal 52 is in contact with the electrode 101a of the ultrasonic transducer 101 by being bent relative to a principal surface of the FPC substrate 50. At this time, the electrode 101a is electrically connected to the lead terminal 52 by, for example, a conductive joining material such as solder. It may also be electrically connected by metallic bonding of electrodes such as in ultrasonic joining. It is preferred that the transducer module 100 be fixed to the FPC substrate 50 with an adhesive and the like at a side surface of the transducer module 100 and at contact surface of the FPC substrate 50.

Subsequently, as illustrated in FIG. 19, after a principal surface of the first extended portion 54 is bent so as to be orthogonal to a principal surface of the circuit formed portion 51, it is bent so as to cover the electrode 101a and the lead terminal 52. Here, as described above, the adhesive is filled between the circuit formed portion 51 and the first extended portion 54 to fix them.

The FPC substrate 50 is electrically connected to the cables 60 with a conductive joining material such as solder, for example, by allowing a conducting wire 61 to be in contact with an electrode 53. Here, as in the first and second embodiments, the second extended portion 55 is bent so as to cover a connection part between the electrode 53 and the conducting wire 61. At this time, as described above, the adhesive is filled between the circuit formed portion 51 and the second extended portion 55 to fix them.

According to the third embodiment, similar to the above-described first and second embodiments, with a simple configuration, it is possible to prevent damage to the lead terminal 52, the electrodes 53 and 101a, and the conducting wire 61 as well as to shield a noise incident from outside and a noise radiated from inside.

In a state where the first extended portion 54 and the second extended portion 55 are bent, by fixing the circuit formed portion 51, the first extended portion 54, and the second extended portion 55 with adhesive and by providing a ground electrode on an outer surface side thereof, a positional relationship between the transducer module 100, the first extended portion 54, the second extended portion 55, and the cables 60 is fixed, whereby it is possible to hold a distance between each of the lead terminals 52 and each of the conducting wires 61 (cables 60), and the ground electrodes formed in the first extended portion 54 and the second extended portion 55 appropriately. Therefore, it is possible to suppress interference between signals transmitted through each of the lead terminals 52 and each of the conducting wires 61 (cables 60), and it is possible to secure required insulation even in a case where the outside of the cable connection structure is damaged.

Note that in the third embodiment, it is possible to combine any of the above-described first and second embodiments and the modified examples as appropriate to connection between the lead terminals and the cables, and the electrodes.

Furthermore, the third embodiment has been described by using the transducer module 100 having a plurality of polygonal column-shaped ultrasonic transducers 101, which is constituted by a piezoelectric element, mounted thereon as an example; however, a similar function and effect can be obtained by the transducer module 100 having a capacitance type ultrasonic transducer, or a Capacitive Micromachined Ultrasonic Transducer (CMUT), mounted thereon. In a case where the CMUT is adopted, unlike a piezoelectric element having a pair of electrodes on a parallel surface, it is possible to configure such that the positive and negative electrodes (wiring part) 101a are disposed on one of surfaces. Therefore, it is possible to cover the wiring part on a signal wire side and on a GND wire side with the extended portion of this embodiment, whereby it is possible to easily secure required insulation. Note that by providing the electrodes (wiring part) on one of the surfaces, visibility is improved, whereby it is possible to realize facilitation of wiring work such as checking of a wiring condition. Therefore, productivity is improved.

Figure 20:
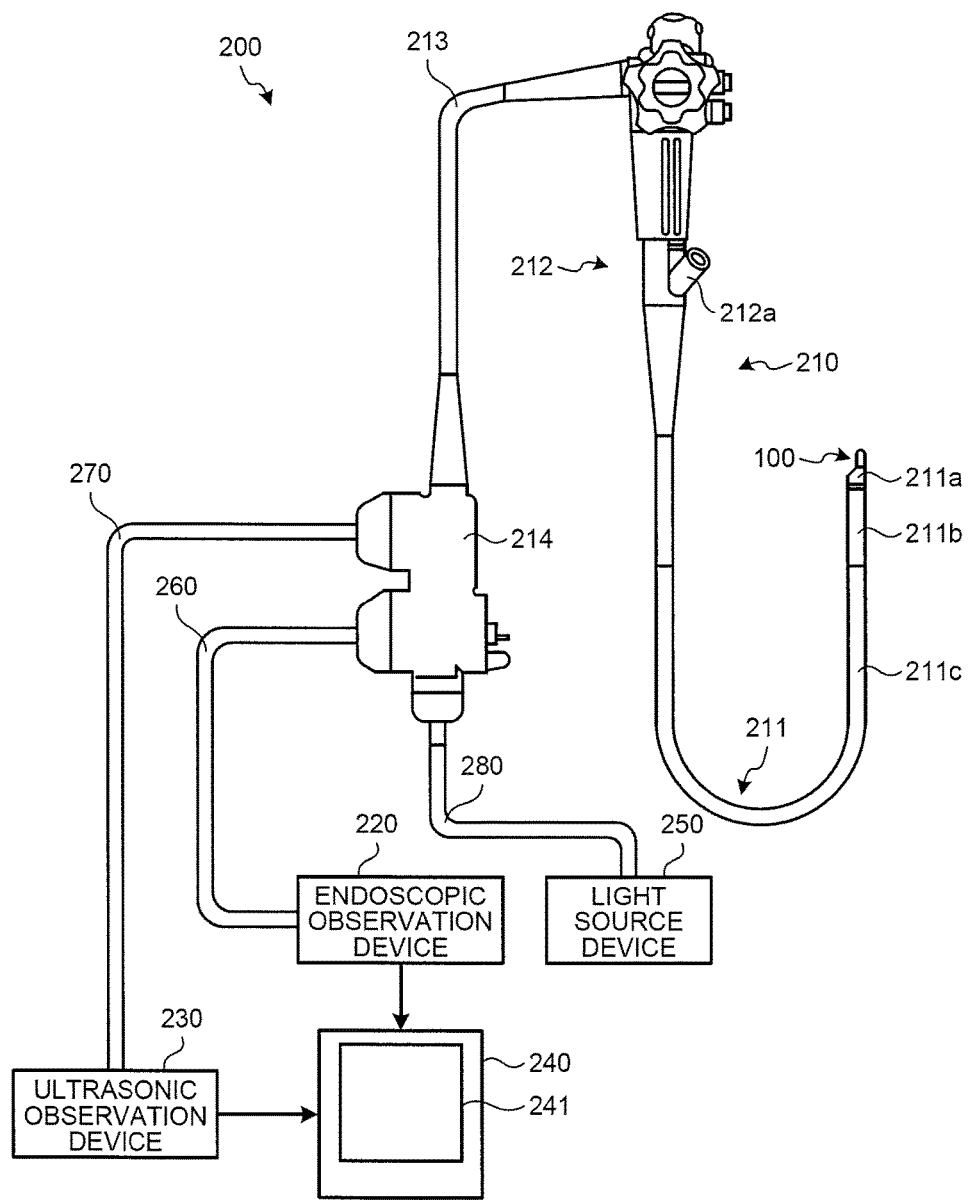
FIG. 20 is a schematic view illustrating an ultrasonic endoscope system using the ultrasonic probe including the cable connection structure according to the third embodiment of the present invention.

The ultrasonic probe 3 according to the above-described third embodiment is provided, for example, at a distal end of an ultrasonic endoscope 210 of an ultrasonic endoscope system 200 illustrated in FIG. 20. The ultrasonic endoscope system 200 illustrated in FIG. 20 is constituted by the ultrasonic endoscope 210, an endoscopic observation device 220, an ultrasonic observation device 230, a display device 240, and a light source device 250.

The ultrasonic endoscope 210 is a convex type ultrasonic endoscope provided with a convex type transducer module 100, and an imaging unit having an observation optical system constituted by a lens and the like and an imaging element. It has an ultrasonic observation function and an endoscopic observation function. Note that the transducer module 100 is realized by the above-described cable connection structure (ultrasonic probe 3). The endoscopic observation device 220 controls the endoscopic observation function and processes an output signal thereof. The ultrasonic observation device 230 controls the ultrasonic observation function and processes an output signal thereof. The display device 240 receives each signal from the endoscopic observation device 220 and the ultrasonic observation device 230, for example, and displays at least one of an endoscopic image or an ultrasonic tomographic image as appropriate. The light source device 250 includes a light source (not illustrated) for supplying illumination light for performing an endoscopic observation. The ultrasonic endoscope system 200 includes a video cable 260, an ultrasonic cable 270, and a light source cable 280 that connect the ultrasonic endoscope 210, the endoscopic observation device 220, the ultrasonic observation device 230, the display device 240, and the light source device 250, respectively.

The ultrasonic endoscope 210 includes an insertion unit 211 which is configured to be inserted into a body of a subject to output an ultrasonic signal inside the body and to obtain the ultrasonic signal reflected from the body, an operational unit 212 which is installed consecutively on a proximal end side of the insertion unit 211, and a universal cable 213 which extends from a side portion of the operational unit 212. The universal cable 213 is provided at an edge portion on a side different from the operational unit 212 side, and has a connector unit 214 which is connected to each of the video cable 260, the ultrasonic cable 270, and the light source cable 280.

The insertion unit 211 is constituted by a distal end hardness unit 211a formed of a hard member, a bending portion 211b configured to be freely bendable, and a flexible pipe unit 211c having flexibility that are connected in order from a distal end side thereof. A proximal end of the flexible pipe unit 211c is connected to a distal end side of the operational unit 212. The above-described transducer module 100 is arranged in a distal end hardness unit 211a.

The operational unit 212 includes a treatment tool insertion opening 212a for introducing a puncture needle, which is a treatment tool, described below and the like into the body. A treatment tool insertion passage is provided inside the insertion unit 211, and the treatment tool insertion opening 212a serves as an insertion opening of the treatment tool insertion passage.

The ultrasonic endoscope 210 is electrically connected to the endoscopic observation device 220 by the video cable 260, which is connected to the connector unit 214. The ultrasonic endoscope 210 is electrically connected to the ultrasonic observation device 230 by the ultrasonic cable 270, which is connected to the connector unit 214. The light source cable 280 is a fiber-optic cable. With regard to the ultrasonic endoscope 210 and the light source device 250, the illumination light from the light source of the light source device 250 is lead to the ultrasonic endoscope 210 through the light source cable 280 connected to the connector unit 214.

In the ultrasonic endoscope system 200 configured as described above, the ultrasonic probe 3 that performs transmission and receiving of an ultrasonic wave is provided at a distal end of the insertion unit 211, and an ultrasonic image of an organ and the like obtained by inserting the insertion unit 211 into the body of the subject is displayed on a display unit 241 of the display device 240, and an in-vivo image captured by the endoscopic observation function is displayed on the display unit 241, whereby it becomes possible to perform observation, diagnosis, and the like of a diagnosis target.

As described above, a cable connection structure, an ultrasonic probe, and an ultrasonic endoscope system according to some embodiments are useful for simply configuring a shield structure and for suppressing interference of signals between cables.

According to some embodiments, because an extended portion is provided that is disposed integrally with a cable or a substrate, extends from the cable or the substrate and covers a connection part between the cable and an electrode, a shield structure can be easily configured and signal interference between the cables can be suppressed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cable connection structure comprising:
   a first substrate formed of a bendable electrically insulating film;
   a plurality of lead terminals that are disposed next to one another along a first direction on the first substrate and projected from an edge portion of the first substrate along a second direction, the second direction being different from the first direction;
   a second substrate having a first surface on which a plurality of electrodes are provided, wherein the plurality of lead terminals are electrically connected to corresponding electrodes of the plurality of electrodes;
   an extended portion that extends from the first substrate along the first direction, and covers the plurality of lead terminals and the plurality of electrodes; and
   an adhesive for joining the extended portion to the second substrate.

2. The cable connection structure according to claim 1, wherein the first substrate includes a bended portion at which the extended portion is bent, and when bent, the extended portion covers the plurality of lead terminals and the plurality of electrodes, the bended portion extending along the second direction.

3. The cable connection structure according to claim 2, wherein the extended portion extends beyond a lead terminal disposed farthermost from the bended portion among the plurality of the lead terminals.

4. The cable connection structure according to claim 1, wherein the extended portion has a length along the second direction, the length being greater than a distance between the edge portion of the first substrate and distal end portions of the plurality of electrodes along the second direction.

5. The cable connection structure according to claim 1, wherein the second substrate is formed of one of a semiconductor and a glass epoxy.

6. The cable connection structure according to claim 1, wherein the first substrate further includes an additional extended portion that extends from the first substrate and covers a second surface of the second substrate, the second surface being opposed to the first surface.

7. The cable connection structure according to claim 1, wherein the second direction is perpendicular to the first direction.

8. The cable connection structure according to claim 1, wherein the plurality of lead terminals are formed of copper.

9. The cable connection structure according to claim 8, wherein surfaces of the plurality of lead terminals are coated with one of nickel and gold.

10. The cable connection structure according to claim 1, wherein the extended portion is provided on an outer surface with a ground electrode to be grounded, the outer surface being opposed to an inner surface facing the first substrate.

11. The cable connection structure according to claim 1, wherein at least one of the first substrate and the extended portion are provided with a ground electrode.

* * * * *